United States Patent [19]

Lihl

[11] Patent Number: 5,048,300
[45] Date of Patent: Sep. 17, 1991

[54] MICROTOME COOLING CHAMBER AND METHOD OF ADJUSTING THE COOLING CHAMBER TEMPERATURE

[75] Inventor: Reinhard Lihl, Vienna, Austria

[73] Assignee: Reichert-Jung Optische Werke A.G., Vienna, Australia

[21] Appl. No.: 523,054

[22] Filed: May 11, 1990

[30] Foreign Application Priority Data

May 26, 1989 [AT] Austria .................................. 1270/89
Apr. 20, 1990 [DE] Fed. Rep. of Germany ....... 4012600

[51] Int. Cl.⁵ .............................................. F17C 7/04
[52] U.S. Cl. ........................................ 62/48.1; 62/320;
83/171; 83/915.5
[58] Field of Search .................... 62/320, 48.1; 83/170,
83/171, 915.5

[56] References Cited

U.S. PATENT DOCUMENTS

| | | | |
|---|---|---|---|
| 3,204,424 | 9/1965 | McCormick et al. | 62/320 |
| 3,218,896 | 11/1965 | McCormick | 83/915.5 |
| 3,233,965 | 2/1966 | McCormick | 83/915.5 |
| 3,236,133 | 2/1966 | De Pas | 83/915.5 |
| 3,462,969 | 8/1969 | Grasenick et al. | 83/915.5 |
| 3,608,324 | 9/1971 | Singleton et al. | 62/48.1 |
| 4,447,952 | 5/1984 | Elkins | 83/170 |
| 4,548,051 | 10/1985 | Moessner | 62/320 |
| 4,657,068 | 4/1987 | Peltz | 83/170 |

*Primary Examiner*—Ronald C. Capossela
*Attorney, Agent, or Firm*—Bean, Kauffman & Spencer

[57] ABSTRACT

A cooling chamber on a microtome has an internal space which is observable and accessible from above and which accommodates an object holder and a tool for processing the object. The cooling chamber structure also includes a supply tank for accommodating a liquid cryogenic agent, the tank communicating with the cooling chamber space by way of a downwardly leading feed conduit for evaporated gaseous cryogenic agent. The feed conduit is directly in the form of a heater which can produce a controllable heating action so that the gaseous cryogenic agent can be heated along its flow path from the tank into the cooling chamber space, to provide for uniform temperature distribution in the cooling chamber space.

13 Claims, 2 Drawing Sheets

MICROTOME COOLING CHAMBER AND METHOD OF ADJUSTING THE COOLING CHAMBER TEMPERATURE

BACKGROUND OF THE INVENTION

In the cryopreparation of objects, in particular biological objects, which are to be subjected to subsequent examination under a microscope or an electron microscope, there is a need for the temperature of the gas atmosphere in the interior of the cooling chamber of a microtome and more particularly an ultramicrotome to be set to a precise value. In that connection, the aim is for it to be possible for the temperature to be set within a relatively wide range going from about −40° C. to about −160° C. While it is relatively easy to set the temperature of the gas atmosphere in the cooling chamber in the vicinity of the lower temperature limit, that is to say around the above-mentioned figure of −160° C., it has been found that problems arise in adjusting the temperature of the gas atmosphere in the middle and upper ranges of temperature in such a way that there is a uniform temperature over the entire space within the cooling chamber of the microtome.

However, many objects require a processing temperature, for example when carrying out a cutting operation thereon, which is in the middle or higher temperature ranges because such objects become brittle at low temperature and do not give a clean cut. The processing temperature can be adjusted by controllable heating resistors in the object holder disposed in the cooling chamber for holding the object to be processed, and in the processing tool itself. However the drain of heat from the cutting region of the processing tool and from the tip of the object being processed, into the cold gas atmosphere in the cooling chamber, can be so great that the cutting edge and the tip of the object are always at a temperature which is close to the temperature of the gas atmosphere.

In an endeavour to deal with that problem, it is possible to heat not only the processing tool and the object holder, but also the gaseous cryogenic agent which fills the interior of the cooling chamber, in accordance with PCT-publication No. WO 88/02851. That is achieved by means of a gas heating plate which is arranged over the floor of the cooling chamber interior in such a way that the gaseous cryogenic agent which passes into the interior of the cooling chamber by issuing from the delivery opening of a feed line opening into the interior of the cooling chamber, can flow away over the heating plate and its temperature is raised as a result.

It has been found however that it is not possible to achieve a satisfactory temperature distribution configuration in respect of the gas atmosphere in the cooling chamber in that way, apparently because only a thin layer of the gaseous cryogenic agent, as it flows over the heating plate, is raised to the desired temperature and rises within the cooling chamber, without effecting uniform temperature distribution therein. In addition, because of the existing temperature gradient troublesome turbulence phenomena may even occur in the gas atmosphere in the cooling chamber, and such turbulence not only interferes with the normal cutting operation to be carried out in the cooling chamber, but it can also permit moist air to penetrate into the interior of the cooling chamber. That moist air then results in frosting on the processing tool and the object so that satisfactory processing of the object is no longer possible under those circumstances.

SUMMARY OF THE INVENTION

An object of the present invention is therefore to provide a cooling chamber on a microtome, which permits more uniform distribution of temperature in the gas atmosphere in the cooling chamber in operation thereof.

Still another object of the present invention is to provide a microtome cooling chamber which permits more sensitive control of the temperature of the gas atmosphere therein and therewith also the processing tool and the object to be processed thereby.

Still another object of the present invention is to provide a method of adjusting the temperature of the gas atmosphere in a cooling chamber of a microtome in such a way as to provide sensitive temperature control and more uniform temperature distribution.

Still a further object of the invention is to provide a microtome having a cooling chamber with a heating arrangement of a simple design configuration effective to provide for sensitive temperature control and uniform temperature distribution within the cooling chamber, without involving major complications in terms of structure and mode of operation.

In accordance with the present invention, in a first aspect, these and other objects are achieved by a cooling chamber on a microtome such as an ultramicrotome, comprising a cooling chamber space which can be observed and is accessible from above. Disposed in the cooling chamber are an object holder for holding an object to be processed and a processing tool for processing the object. The arrangement further includes a supply tank for accommodating a liquid cryogenic agent such as $LN_2$, which is communicated with the space in the cooling chamber by way of a feed line opening thereinto for supplying the cooling chamber with evaporated gaseous cryogenic agent, together with a heatable element in the flow path of the gaseous cryogenic agent for setting a predetermined temperature in respect of the gas atmosphere in the cooling chamber space. The heatable element is a heater means forming the feed line itself.

In accordance with another aspect of the invention, the foregoing and other objects are achieved by a method of setting the temperature of the gas atmosphere in the cooling chamber space on a microtome, wherein gaseous cryogenic agent which evaporates from a supply of liquid cryogenic agent is passed into the interior of the cooling chamber, with the gaseous cryogenic agent being heated in its feed flow path from the supply thereof into the cooling chamber.

The invention thus involves the consideration that heating of the gaseous cryogenic agent which has already passed into the cooling chamber is to be avoided and on the contrary only gaseous cryogenic agent at a uniform temperature is to be allowed to flow into the cooling chamber. As constructions according to the invention provide that the feed line leading from the top side of the supply tank for the liquid cryogenic agent to the bottom of the interior of the cooling chamber is itself in the form of a heater body and completely encloses the evaporated gaseous cryogenic agent on its way into the cooling chamber, there is sufficient time and distance involved in that design configuration to provide for totally uniform heating of the flow of gaseous cryogenic agent to the inlet opening of the feed line into the cooling chamber. In that connection, the transfer of heat to the flow of cryogenic gas in the interior of the heater body can be specifically controlled by for example the flow cross-section of the line being of a suitable configuration. Thus the heater body may extend over the entire width of the cooling chamber along one wall thereof, at the location where the feed line opens into the cooling chamber, and the interior thereof, which forms the flow cross-section for the gaseous cryogenic agent, may be of a corresponding design configuration, thus providing a large heat transfer surface area so as to ensure uniform heating of the flow of gas. An additional design feature may provide that the feed flow path for the gaseous cryogenic agent is of a zig-zag or meanderlike configuration in the interior of the heater body, so that the effective length thereof is accordingly increased.

In a preferred feature of the invention, the mouth opening in the heater body, from which the gaseous cryogenic agent passes into the cooling chamber, is preferably of a slot-like configuration and extends at least approximately parallel to the bottom of the cooling chamber, at a small spacing above same. In principle one such mouth opening is sufficient, but it may be advantageous to provide a plurality of such mouth openings, in the side wall of the heater body which is towards the interior of the cooling chamber, the mouth openings being for example in the form of slots which extend parallel to each other in superposed relationship, or in the form of a perforation. In that way it is possible to produce horizontal, virtually laminar flow layers in the interior of the cooling chamber, which result in a correspondingly smooth and stable flow condition.

Regulating the temperature of the heater body makes it possible to adjust the temperature of the in-flowing gaseous cryogenic agent to the desired value so as to ensure the minimum possible temperature gradient between a processing tool disposed in the cooling chamber and the object to be processed thereby.

Further objects, features and advantages of the invention will be apparent from the following description of preferred embodiments thereof.

DESCRIPTION OF PREFERRED EMBODIMENTS

Figure 1:
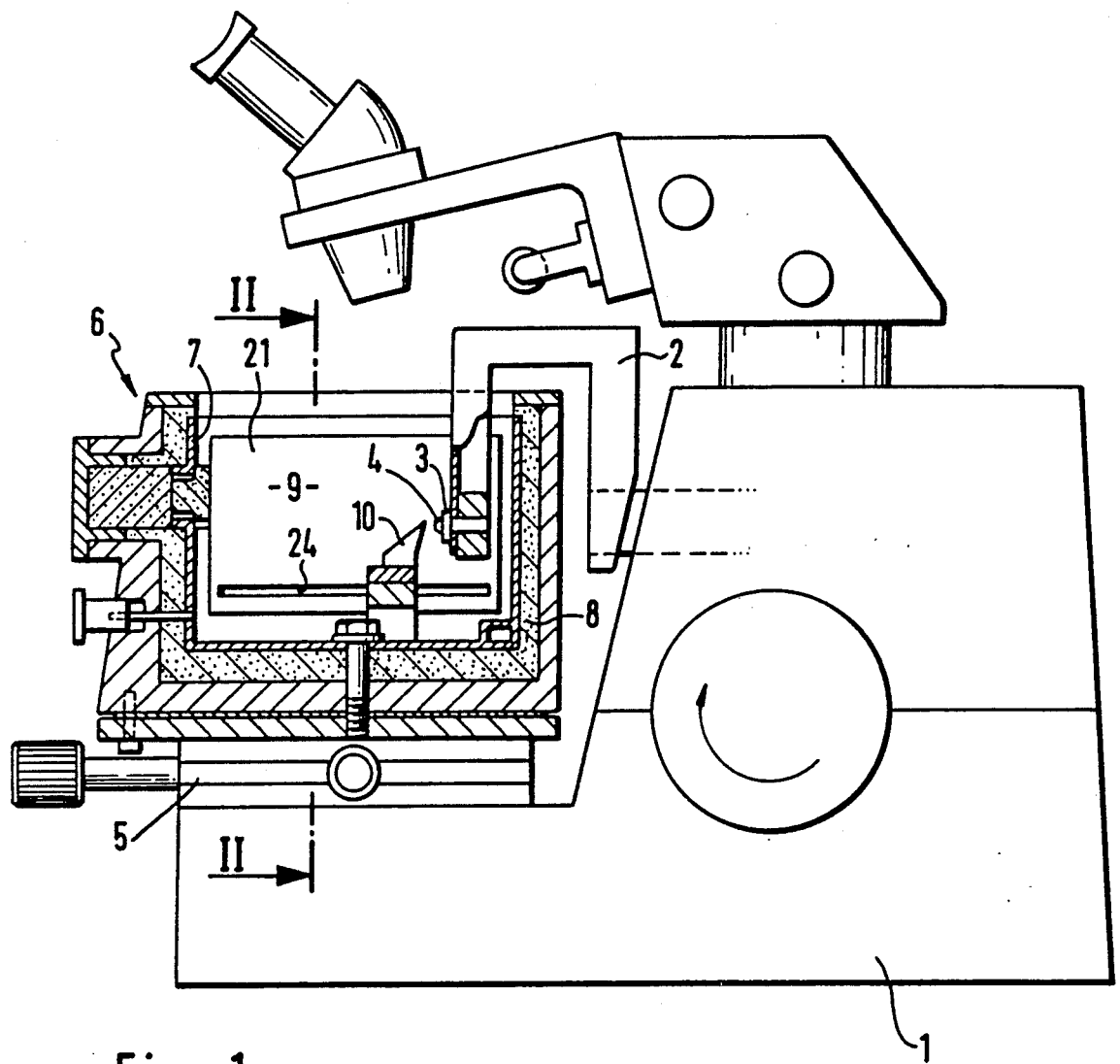
FIG. 1 is a side view of an ultramicrotome, partly in section in the region of the cooling chamber thereof.

Referring firstly to FIG. 1, shown therein is a microtome and more specifically an ultramicrotome 1 having an object support arm 2 in the form of a device which is known as a CHRISTENSEN bridge. Arranged at the forward end of the support arm 2 is an object holder 3 for a biological object 4 which is to be subjected to processing. Fixed on the support 5 of the ultramicrotome 1 is a cooling chamber which is generally identified by reference numeral 6 and which is substantially of a box-like configuration, comprising an inside wall 7 which is of a material which is a good conductor of heat, and which is enclosed on all sides on the outside thereof by a layer 8 of heat-insulating material. A processing tool 10 in the form of a knife is arranged in the interior 9 of the cooling chamber 6 in such a way that sections of the object 4 can be produced upon upward and downward movements of the object 4 relative to the knife 10. The structure of the ultramicrotome 1 and the mode of operation thereof, in regard to a cutting procedure, are of generally conventional nature and therefore do not need to be described in greater detail herein.

Figure 2:
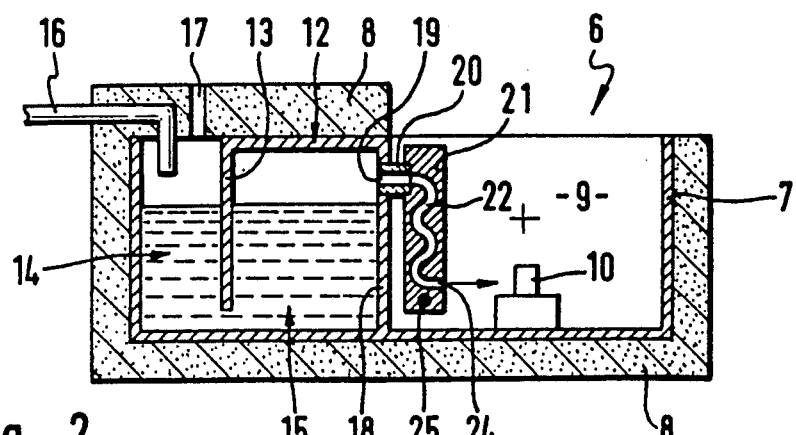
FIG. 2 is a view in cross-section through the cooling chamber in FIG. 1 taken along line II—II therein, with the other components of the ultramicrotome not being shown for the sake of enhanced clarity of the drawing.

Referring now to FIG. 2 which is only a diagrammatic view of the cooling chamber 6 of the ultramicrotome 1 in FIG. 1, the left-hand part of the cooling chamber 6 forms a supply tank 12 for a liquid cryogenic agent, preferably liquid nitrogen ($LN_2$); the tank 12 is also covered on the top side thereof by the layer 8 of heat-insulating material. A partitioning wall 13 in the supply tank 12, which extends downwardly thereinto to a position close to the bottom of the supply tank 12, divides the interior thereof into a refilling portion 14 and an evaporator portion 15. Further $LN_2$ can be introduced into the refilling portion 14 through a refilling conduit 16, as required. Turbulent gas flows which can occur in a refilling operation are removed by way of a small opening 17 in the heat-insulating layer 8 and therefore cannot affect the temperature equilibrium in the interior 9 of the cooling chamber 6.

The supply tank 12 extends over the entire width of the interior 9 of the cooling chamber and has a slot-like communicating opening 19 above the level of the $LN_2$, at the cooling chamber side wall 18 which is towards the interior 9 of the cooling chamber. A short connecting conduit 20 of a material which is a poor conductor of heat is connected to the communicating opening 19 in a manner not shown in the drawing. A heater body 21 is fixed to the outer end of the conduit 20, also in a manner not shown in the drawing. The heater body 21 is substantially in the form of a flat or shallow parallelepiped and, as can be seen from FIG. 1, extends substantially over the width of the interior 9 of the cooling chamber 6. It also forms the feed line or conduit for the gaseous nitrogen which evaporates from the $LN_2$ to the interior 9 of the cooling chamber and for that purpose has a hollow interior as indicated at 22, which leads to a mouth opening 24 arranged in the lower part of the interior 9 of the cooling chamber 6. The flow cross-section of the feed conduit 22 is of a rectangular slot-like configuration, corresponding to the slot shape of the mouth opening 24 which extends substantially parallel to the floor of the interior 9 of the cooling chamber 6. As shown in FIG. 2, in order to increase the flow path length, the feed conduit 22 also extends in a loop-like or zig-zag configuration in the interior of the heater body 21.

Disposed in the lower portion of the heater body 21 is a heating resistor 22 which holds the heater body 21 to an adjustable temperature, by a suitable regulating means (not shown).

If it is necessary for an object 4 to be cut at a given temperature which is in a medium temperature range of for example $-80°$ C., then a desired temperature is set at the object object holder 3 and in the processing tool 10 by means of heating resistors (not shown) disposed in the object holder 3 and in the processing tool 10. The supply of heat to produce that predetermined temperature is also effected under the control of a suitable regulating means (not shown), in conventional manner. The heater body 21 is also heated to a given desired temperature by suitable heating of the heating resistor 25. The gaseous nitrogen which evaporates from the surface of the $LN_2$ is urged out of the closed evaporator portion 15 into the heater body 21 and flows downwardly through same to the mouth opening 24. On the way to that location, the gaseous nitrogen absorbs heat from the walls of the heater body 21 so that its temperature is increased to the desired value. Sensors (not shown) in the interior 9 of the cooling chamber can monitor the temperature of the gaseous nitrogen issuing from the mouth opening 24, and suitably regulate the heating output of the heating resistor 25. As the interior 9 of the cooling chamber receives a flow of only uniformly heated nitrogen gas, a uniform temperature distribution occurs therein.

Figure 3:
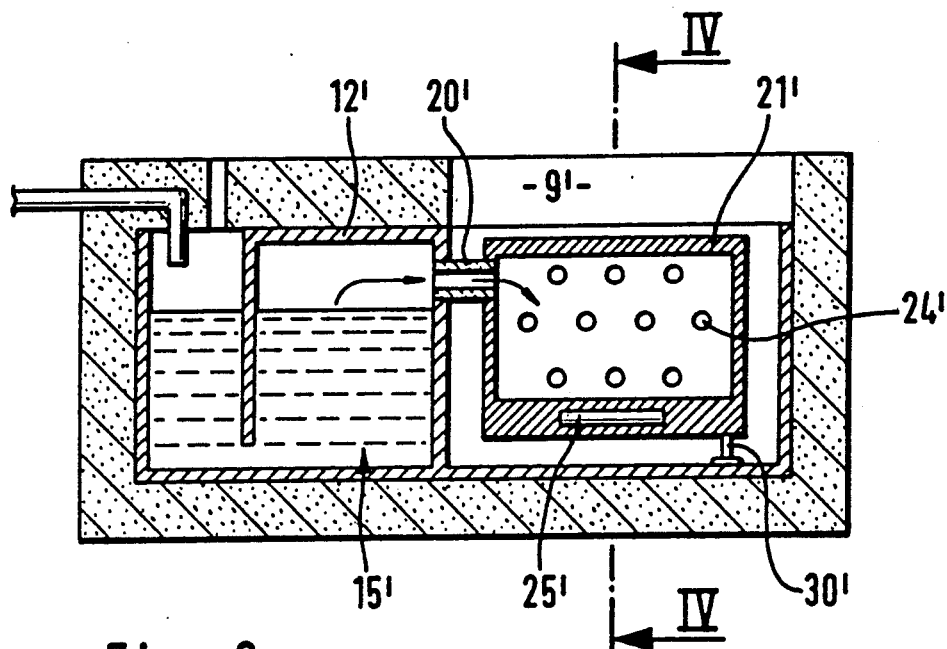
FIG. 3 is a view in section similar to that shown in FIG. 2 through a modified embodiment of the cooling chamber according to the invention.
Figure 4:
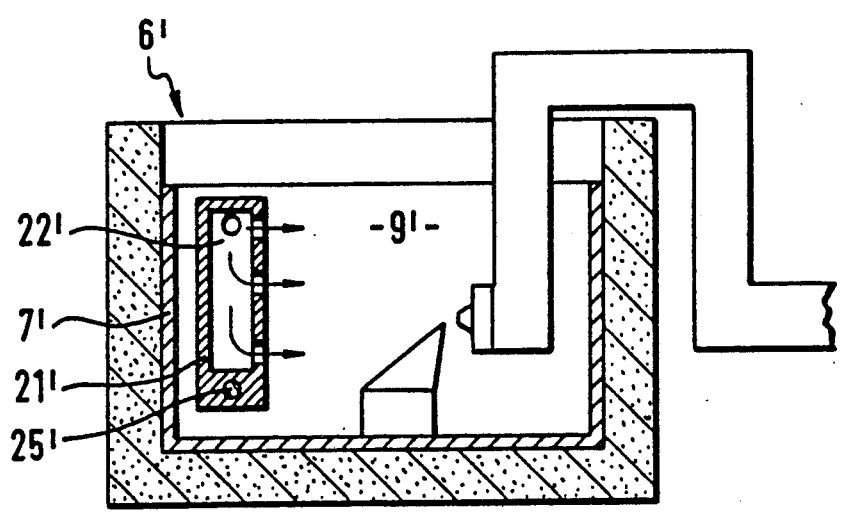
FIG. 4 is a view in section taken along line IV—IV in FIG. 3.

Reference will now be made to FIGS. 3 and 4 showing an embodiment which differs from that illustrated in FIGS. 1 and 2 only in regard to the configuration and arrangement of the heater body 21'. In other respects the design configuration of the cooling chamber is identical to that shown in FIGS. 1 and 2 so that there is no need for a further detailed description in respect thereof.

The heater body 21' is substantially parallelepipedic and faces with its narrow sides towards the supply tank 12', in other words, it is arranged along one of the walls 7' of the cooling chamber 6'. In that way, when the heater body 21' produces a heating effect, a smaller amount of heat is given off to the supply tank 12' by radiation. The heater body 21' is supported by a support element 30' of material which is a poor conductor of heat, on the floor of the interior 9' of the cooling chamber, and is connected to the evaporator portion 15' by way of a pipe connecting portion 20' which is a poor conductor of heat.

The interior of the heater body 21' which once again forms the feed conduit for the gaseous nitrogen is substantially also parallelepipedic. It communicates with the interior 9' of the cooling chamber by way of an array of holes 24' provided in the side wall of the heater body 21', which is towards the interior 9' of the cooling chamber. The mouth openings formed by the holes 24' are arranged in three rows one above the other so that the gaseous nitrogen which flows in the heater body 21' can issue through each row of holes and can flow into the interior 9' of the cooling chamber, as indicated by arrows in FIG. 4. That provides a laminar flow configuration which results in uniform temperature distribution in the gas atmosphere in the interior 9' of the cooling chamber.

The heater body 21 in FIGS. 1 and 2 and 21' in FIGS. 3 and 4 comprises a material which is a good conductor of heat, at least in the part of its walls which form the feed conduit for the gaseous nitrogen. On the other hand, in order to prevent heat being given off to the atmosphere in the cooling chamber, the outside surfaces of the heater body 21 or 21' may be coated with or formed from a material which is a poor conductor of heat.

It will be noted at this point that in the illustrated embodiment of the microtome cooling chamber the internal space 9 or 9' thereof is observable and accessible from above, while the feed conduit 22 or 22' which communicates the supply tank with the interior of the cooling chamber structure leads in a downward direction.

It will be appreciated that the above-described embodiments and procedure have been set forth solely by way of example and illustration and that various modifications and alterations may be made therein without thereby departing from the spirit and scope of the invention.

What is claimed is:

1. A cooling chamber on a microtome comprising an internal space which is observable and accessible from above for accommodating in said space an object holder for holding an object to be processed and a processing tool for the object, with heating resistance means for controlling the temperature of the object holder and the processing tool to a desired value, and further including a supply tank for accommodating a liquid cryogenic agent, and a heater body providing a feed conduit communicating the tank with the cooling chamber space and opening into the cooling chamber space to feed evaporated gaseous cryogenic agent thereto, the heater body being operable to heat the gaseous cryogenic agent as it flows to said cooling chamber space for setting a predetermined temperature of the gas atmosphere in the cooling chamber space.

2. A cooling chamber as set forth in claim 1 wherein the heater body has at least one mouth opening for delivery of the gaseous cryogenic agent into the cooling chamber space in a side wall of the heater body which is directed towards the cooling chamber space.

3. A cooling chamber as set forth in claim 1 wherein said heater body has a side wall directed towards the cooling chamber space, and a plurality of mouth openings for delivery of the gaseous cryogenic agent into the cooling chamber space, which mouth openings are arranged in superposed relationship.

4. A cooling chamber as set forth in claim 2 wherein said at least one mouth opening is of a slot configuration extending at least approximately parallel to the bottom of the cooling chamber space.

5. A cooling chamber as set forth in claim 3 wherein said mouth openings are of a slot configuration extending at least approximately parallel to the bottom of the cooling chamber space.

6. A cooling chamber as set forth in claim 2 wherein said at least one mouth opening comprises a plurality of holes arranged in side-by-side relationship in a line which is at least approximately parallel to the bottom of the cooling chamber space.

7. A cooling chamber as set forth in claim 3 wherein each said mouth opening comprises a plurality of holes arranged in side-by-side relationship in a line which is at least approximately parallel to the bottom of the cooling chamber space.

8. A cooling chamber as set forth in claim 1 wherein the heater body has an internal space which forms a flow path for the gaseous cryogenic agent, the heater body and its internal space extending substantially over the width of the cooling chamber space.

9. A cooling chamber as set forth in claim 1 wherein the feed conduit for the gaseous cryogenic agent extends in a zig-zag configuration in the interior of the heater body.

10. A cooling chamber as set forth in claim 1 wherein the heater body has a lower part accommodating a controllable heating resistor means.

11. A cooling chamber as set forth in claim 1 including a connecting conduit which is a poor conductor of heat, connecting the supply tank to the heater body.

12. A cooling chamber as set forth in claim 1 wherein the heater body is substantially parallelepipedic and has a narrow side facing towards the supply tank.

13. A microtome including a cooling chamber structure providing an internal space observable and accessible from above, for accommodating an object holder to hold an object to be processed and a processing tool for processing the object, the cooling chamber structure further including a supply tank for accommodating a liquid cryogenic agent, and a conduit means communicating the supply tank with the cooling chamber space and opening into the cooling chamber space adjacent to the bottom thereof to feed cryogenic agent in gaseous form from evaporation of the liquid cryogenic agent accommodated in the supply tank into said cooling chamber space, at least a portion of the conduit means being constituted by a heater means operable to heat said gaseous cryogenic agent as it flows therethrough from said supply tank to said cooling chamber space.

* * * * *